(12) United States Patent
Meyer et al.

(10) Patent No.: US 11,674,940 B2
(45) Date of Patent: Jun. 13, 2023

(54) SYSTEM AND METHOD TO AVOID THE INFLUENCE OF OZONE FOR A GAS SENSOR

(71) Applicant: Renesas Electronics America Inc., Milpitas, CA (US)

(72) Inventors: Christian Meyer, Dresden (DE); Debra Deininger, Longmont, CO (US); Clayton Kostelecky, Longmont, CO (US); Ronald Schreiber, Freital (DE); Holger Saalbach, Radebeul (DE); Ravi Kanth Reddy Chilumula, Longmont, CO (US)

(73) Assignee: Renesas Electronics America Inc., Milpitas, CA (US)

( * ) Notice: Subject to any disclaimer, the term of this patent is extended or adjusted under 35 U.S.C. 154(b) by 66 days.

(21) Appl. No.: 17/122,761

(22) Filed: Dec. 15, 2020

(65) Prior Publication Data
US 2021/0190750 A1    Jun. 24, 2021

Related U.S. Application Data

(60) Provisional application No. 62/952,841, filed on Dec. 23, 2019.

(51) Int. Cl.
*G01N 33/00* (2006.01)

(52) U.S. Cl.
CPC ..... *G01N 33/0039* (2013.01); *G01N 33/0016* (2013.01)

(58) Field of Classification Search
CPC .......... G01N 33/0039; G01N 33/0016; G01N 27/12; G01N 27/123; G01N 27/416; Y02A 50/20
See application file for complete search history.

(56) References Cited

U.S. PATENT DOCUMENTS

| 4,885,929 A * | 12/1989 | Kasahara | G01N 33/0039 73/31.06 |
| 9,823,211 B1 * | 11/2017 | Allen | G01N 33/0031 |
| 2009/0120212 A1 * | 5/2009 | Hargrove | G01N 33/0037 73/863.11 |
| 2019/0234896 A1 * | 8/2019 | Andersson | G01N 33/0014 |
| 2019/0242841 A1 * | 8/2019 | Meyer | G01N 33/0009 |

* cited by examiner

*Primary Examiner* — Francis C Gray
(74) *Attorney, Agent, or Firm* — Haynes and Boone, LLP

(57) ABSTRACT

In some embodiments, a method of operating a gas sensor includes setting power to a heater in contact with a MOx sensor to provide a temperature that is below a threshold temperature; holding the temperature below the threshold temperature for a period of time to reduce ozone concentration in a gas sample in contact with the MOx sensor; increasing power to the heater to increase the temperature of the MOx sensor to an operating temperature; acquiring resistance data from the MOx sensor at the operating temperature; and processing the resistance data to provide a result related the gas sample.

20 Claims, 14 Drawing Sheets

SYSTEM AND METHOD TO AVOID THE INFLUENCE OF OZONE FOR A GAS SENSOR

RELATED APPLICATION

The present application claims priority to U.S. Provisional Application Ser. No. 62/952,841, filed on Dec. 23, 2019, which is herein incorporated by reference in its entirety.

TECHNICAL FIELD

Embodiments of the present invention are related to position sensors and, in particular, to a system and method to avoid the influence of ozone in a gas sensor.

DISCUSSION OF RELATED ART

Measuring the presence of volatile organic compounds (VOC) has gained increased importance due to the widespread occurrence of VOCs and the resulting need to monitor air quality for those VOCs. In particular, the indoor air quality (IAQ) can be affected by a large number of air contaminates, including from cooking, materials off-gassing, scented candles, perfume and other cosmetics, and exhaust gas emissions. Gas sensors can be used for indoor air quality (IAQ) monitoring, or air quality monitoring in general, including estimated CO2 (eCO2) monitoring and total volatile organic compounds (TVOC).

MEMs-based sensors have been developed that promise gas sensors with smaller sizes, lower process, and embedded signal conditioners for ease of use and integration. This class of gas sensors can allow gas sensing technology to be incorporated within a wide range of devices, including mobile, wearable, and Internet-of-Things (IOT) devices, and do not require specialized experience to operate. These gas sensing technologies can include a heater element and a metal oxide (MOx) chemiresistor. The circuitry controls the sensor temperature and measures the MOx conductivity, which is a function of the gas concentrations.

In general, the MOx resistor is heated to an operating temperature. The resistance of the MOx resistor is sensitive to impurity gas concentrations in the air. The change in resistance from a baseline is based on gas type and concentration and can increase or decrease, depending upon the MOx materials used and the type of impurity gas present. For example, resistance range can increase greatly during an event with oxidizing gases such as ozone or decrease upon exposure to VOCs. The resistance increase during an ozone event might lead to a competing reaction to the desired VOC response, or a shift in baseline, underreporting (IAQ/TVOC) during ozone events, and wrong algorithm reporting after ozone (IAQ/TVOC/eCO2). An ozone event can occur during air exchanges with ozone enriched outdoor air, for example.

Therefore, there is a need to develop better sensing designs for gas sensors that are more resistant to ozone events.

SUMMARY

In some embodiments, a method of operating a gas sensor includes setting power to a heater in contact with a MOx sensor to provide a temperature that is below a threshold temperature; holding the temperature below the threshold temperature for a period of time to reduce ozone concentration in a gas sample in contact with the MOx sensor; increasing power to the heater to increase the temperature of the MOx sensor to an operating temperature; acquiring resistance data from the MOx sensor at the operating temperature; and processing the resistance data to provide a result related the gas sample.

In some embodiments, a gas sensor includes a MOx sensor; a heater in contact with the MOx sensor; a heater driver configured to control the heater; a processor configured to receive resistance data from the MOx sensor, control the heater driver to control a temperature of the MOx sensor, and further configured to execute instructions to set power to a heater in contact with a MOx sensor to provide a temperature that is below a threshold temperature; hold the temperature below the threshold temperature for a period of time sufficient to reduce ozone concentration in a gas sample below a threshold concentration; increase power to the heater to increase the temperature to an operating temperature; acquire resistance data from the MOx sensor at the operating temperature; reduce power to the heater to reduce the temperature below the threshold temperature; and process the resistance data to provide a result related the gas sample.

These and other embodiments are discussed below with respect to the following figures.

These and other aspects of embodiments of the present invention are further discussed below.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description illustrates inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

In accordance with embodiments of the present invention, a sequence with a low temperature step to allow the ozone to react, while other gases are not reacting at this temperature. As a result, this low temperature step can greatly reduce the interference in gas concentration measurements resulting from the effects of an ozone concentration. Procedures according to the present invention are advantageous because real measurements can be made without the need for additional filtering or with an algorithm that adjusts signals based on the last plausible resistive values while ignoring the high resistances that result from the presence of ozone.

Figure 1A:
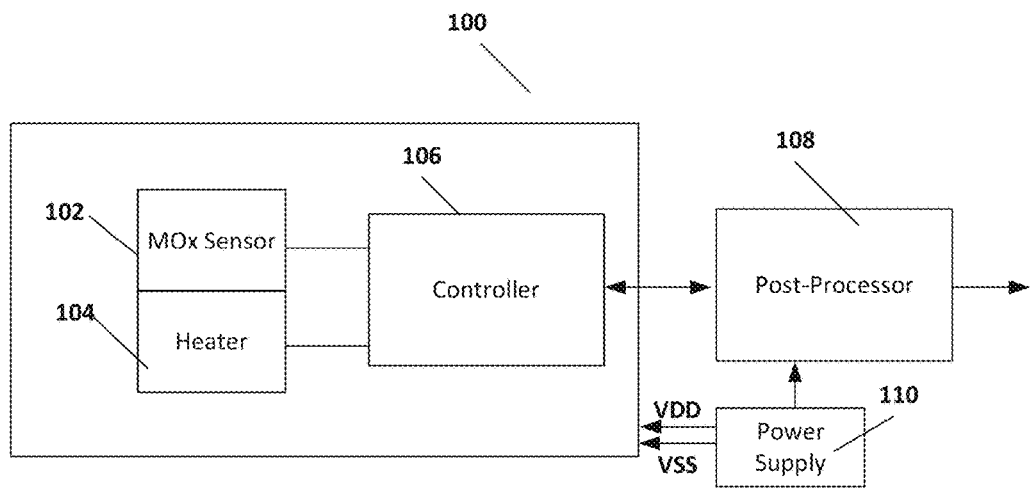
FIGS. 1A through 1C illustrates aspects of a gas sensor on which embodiments of the present disclosure can be implemented.

FIG. 1A illustrates a gas sensor 100 on which aspects of the present disclosure can be implemented. As illustrated in FIG. 1A, gas sensor 100 includes a metal oxide (MOx) sensor 102 thermally coupled to a heater 104. As discussed above, MOx sensor 102 has a conductivity that is sensitive to the presence of various gasses, particularly volatile organic compounds (VOC). VOCs refer to a family of high vapor pressure and low water-solubility chemicals that often resulting from manufacturing, combustion, out-gassing, or cleaning materials. These VOCs often present health risks and consequently a great interest in monitoring VOCs to provide a measurement of air quality has developed. VOCs include, for example, industrial solvents, fuel oxygenates, by-products of chlorination in water treatment, and are components of petroleum fuels, hydraulic fluids, paint thinners, dry cleaning agents, and other such products. As discussed above, the conductivity of the MOx sensor 102 is dependent on presence of these materials in the sampled gas. Consequently, gas sensor 100 including MOx sensor 102 can be configured to detect total VOCs (TVOCs), can be used to estimate CO2, and can be used for monitoring indoor air quality (IAQ).

However, the operation of MOx sensor 102 can be affected by the presence of oxidizing gasses, including the presence of ozone. The presence of ozone can affect the base line and accuracy of the detection of VOCs in the air samples. Aspects of the present disclosure provide for a gas sensor 100 that can mitigate the negative aspects of any ozone that may be present in the sampled gas.

As illustrated in FIG. 1A, MOx sensor 102 is mounted on a heater 104, which controls the operating temperature of MOx sensor 102. Heater 104 can, for example, be formed with silicon micromachining to create a robust, thermally isolated micro-hotplate (MHP) on which MOx sensor 102 is formed. The operating temperature T can range over a large range and affects the sensitivity of MOx sensor 102. In some embodiments, the operating temperature can range, for example, between 100 and 500° C.

As further illustrated in FIG. 1A, heater 104 and MOx sensor 102 are coupled to a controller 106. Controller 106 includes a combination of analog and digital circuitry to monitor the conductivity of MOx sensor 102 while controlling the temperature of MOx sensor 102 through heater 104. Controller 106 may include memory and processors that process the data received from MOx sensor 102. Further, controller 106 may provide processed data to a post processor 108 coupled to gas sensor 100. Controller 106, as discussed below, includes memory and processors capable of operating algorithms as discussed here. Post-processor 108 receives the processed data from controller 106. Post-processor 108 may further provide data and instructions executable within controller 106 to control heater 104 and measure signals from MOx sensor 102 and process those signals.

As is further illustrated in FIG. 1A, a power supply 110 provides power for both post processor 108 and gas sensor 100. In some embodiments, gas sensor 100, post processor 108, and power supply 110 can be mounted on a single printed circuit board. However, in some embodiments, these components may be separated.

Figure 1B:
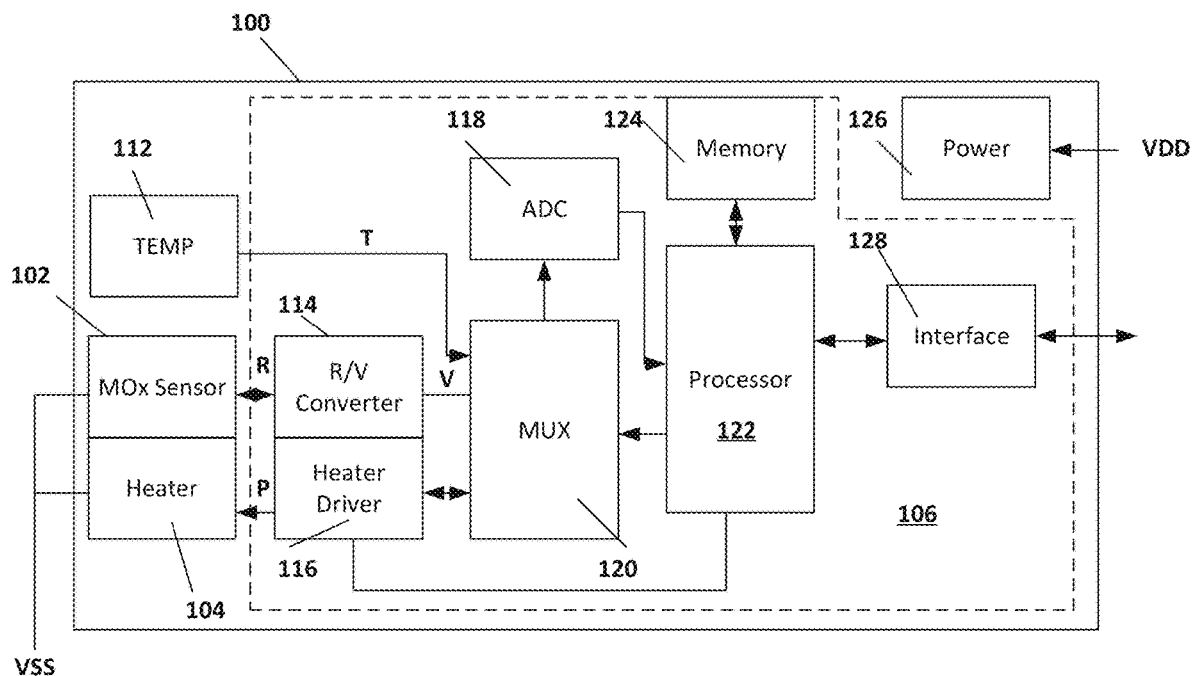

FIG. 1B illustrates gas sensor 100 in further detail. As shown in the example illustrated in FIG. 1B, controller 106 of gas sensor 100 includes a converter 114, a heater driver 116, an analog-to-digital converter 118, a processor 122, memory 124, and a communications interface 128. Converter 114 determines the conductivity of MOx sensor 102 and provides a voltage V that indicates the resistance of MOx sensor 102. In some embodiments, the resistance R can be determined by providing a particular current through MOx sensor 102 and measuring the voltage V across MOx sensor 102.

Heater driver 116 is coupled to control heater 104. Heater driver 116 is driven controlled by processor 122 to driver heater 104 to control the temperature of MOx sensor 102. In some embodiments, a temperature sensor 112 may be provided to determine the temperature T of MOx sensor 102. In some embodiments, the temperature T of MOx sensor 102 may be determined by the power provided to driver heater 104, which may have a determined relationship between power and the temperature T of MOx sensor 102.

Analog-to-digital converter (ADC) 118 of controller 106 digitizes signals for input to processor 122. In some embodiments, ADC 118 may include a plurality of ADCs to digitize various signals. ADC 118 can include ADCs of any resolution appropriate for the sensitivity of gas sensor 100. In the example illustrated in FIG. 1B, signals are input to a multiplexer 120 and processor 122 selects a signal for digitization in ADC 118. As illustrated in FIG. 1B, the voltage indicating the resistance of MOx sensor 102 from converter 114, a temperature T from temperature sensor 112, and a power indication P from heater driver 116 may be input to multiplexer 120 for digitization by ADC 118 and input to processor 122.

Processor 122 can include any microcontroller, microcomputer, microprocessor, or other digital processing circuit that is capable of executing the instructions as described here. Processor 122 is coupled to a memory 124. Memory 124 includes volatile and non-volatile memory sufficient to hold data and instructions to be executed by processor 122. Processor 122 is coupled to select signals for digitization in multiplexer 120, is coupled to receive digitized signals from ADC 118, and is further coupled to control the power to heater 104. Processor 122 may, in some embodiments, include a combination of digital processors as described above and analog circuits, as discussed further below, to perform calculations according to some aspects of the present disclosure.

As is further illustrated in FIG. 1B, processor 122 may be coupled to an interface 128. Interface 128 may include any protocol such as I2C, GPIO, USB, or other protocol for transmitting and receiving digital data with an external device such as post processor 108 illustrated in FIG. 1A.

As is further illustrated in FIG. 1B, a power block 126 receives the voltage Vdd and supplies power for gas sensor 100. In some embodiments, gas sensor 100 can be formed on a single integrated circuit (IC). In some embodiments, gas sensor 100 may be discreet components.

Figure 1C:
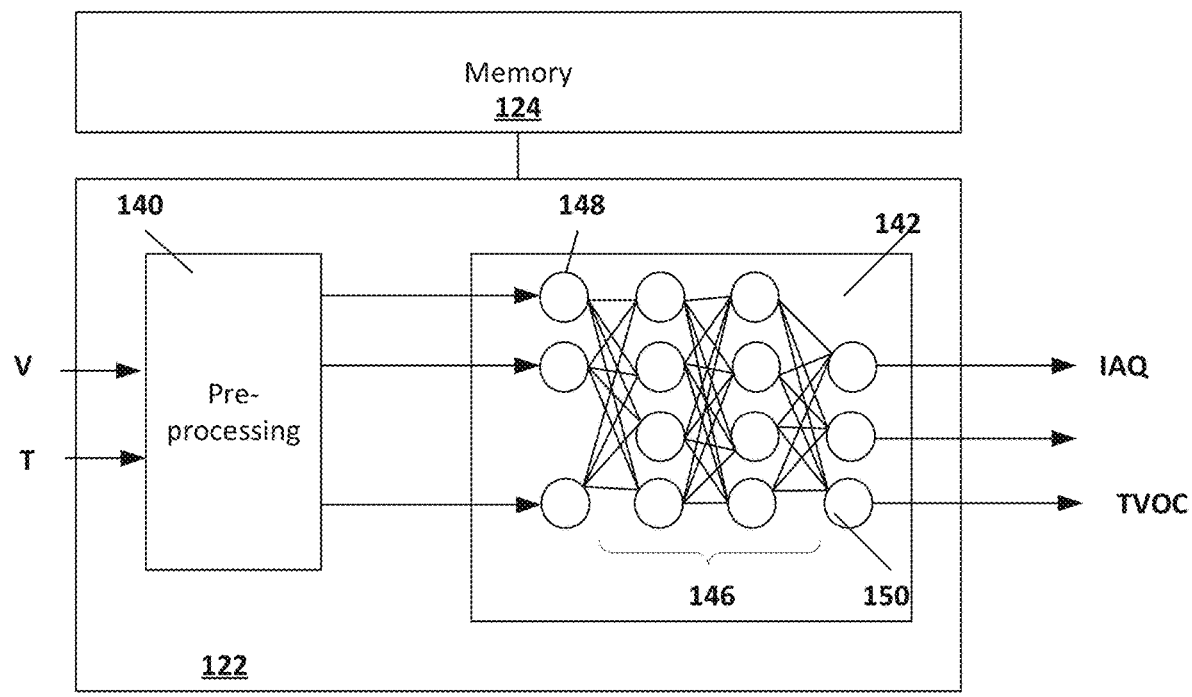

In some embodiments according to this disclosure, a neural network artificial intelligence 142 may be implemented in processor 122 to process data to provide results related to the gas sample at MOx sensor 102. A preprocessor 140 may receive parameters such as the voltage signal V indicating the resistance of MOx sensor 102 and an indicating of the operating temperature of MOx sensor 102, T, and process those parameters to provide gas related results such as TVOC concentration, estimated CO2 concentrations, indoor air quality, or even individual VOC concentrations. FIG. 1C illustrates an example of processor 122 with neural network processing. As illustrated in FIG. 1C, processor 122 can execute instructions to provide pre-processing 140, which receives the raw data and pro-processes the data (e.g., provide digital filtering, initial calculations, or other processing) to provide data to AI processing, or neural network, 142. As illustrated in FIG. 1C, AI processing may be a neural network 142. The main components of neural network 142 are input nodes 148 that receives the data from pre-processing 140, nodes in hidden layers 146 where data is processed by sequentially applying weighted functions to process data and pass to the next layer. Finally, output nodes 150 provided the results. The weighted parameters of each of the functions executed in each of the nodes can be set by a training algorithm that rely on a training data set. Memory 124 is large enough to store the weighting parameters for operation of neural network 142. In some cases, neural network 142 may be, at least partially, trained in a supervised learning method where gas sensor 100 processes a set of known gas samples to set the weighting parameters. In either case, neural network 142 may provide much more reliable results for the gas dependent results output by gas sensor 100.

Neural network 142 can be implemented digitally in processor 122 or may be implemented in analog circuits in processor 122. In some embodiments the weighting factors to each node may be digitized and the nodes of neural network 142 may be implemented by analog circuitry. Whether processing in each node is performed digitally or by analog circuits, the weighting factors are stored in memory 124 and coupled to each of the nodes of input nodes 148, hidden layers 146, and output nodes 150.

As is discussed above, processor 122, through heater driver 104, controls the temperature of MOx sensor 102 by controlling heater 104. In accordance with embodiments of the present disclosure, the temperature on MOx sensor 102 is controlled to have a low temperature portion where the temperature of MOx sensor 102 is held at a temperature below a threshold temperature for a period of time sufficient to allow the ozone to react and reduce the ozone concentration below a threshold concentration before increasing the temperature to an operating temperature.

The resistance of MOx sensor 102 can generally be modeled as a function of the gas concentration at the sensor. In particular, the resistance of MOx sensor 102 can follow a power law behavior illustrated by $$R_{MOx} = Ac^{-\alpha}$$

Where $R_{MOx}$ is the resistance of MOx sensor 102, c is the gas impurity concentration, and A and $\alpha$ are material dependent parameters. The sensitivity of the resistance of MOx to various VOC concentrations can be dependent on the operating temperature of MOx sensor 102. The IAQ determination can be determined from the gas concentration, for example by mapping the concentration of VOCs to particular IAQ values.

Figure 2:
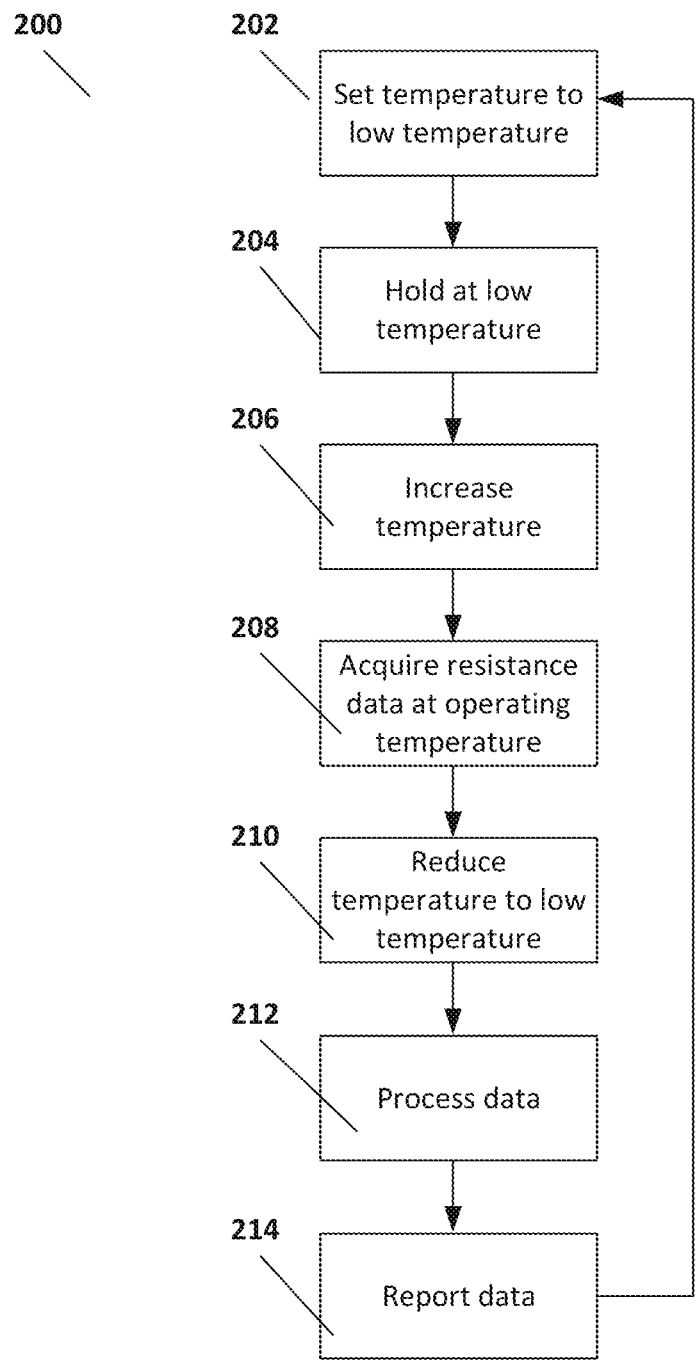
FIG. 2 illustrates an example process for operating the gas sensor according to aspects of the present disclosure.

FIG. 2 illustrates a process 200 for operating a gas sensor 100 according to some embodiments of the present disclosure. As illustrated in FIG. 2, process 200 starts in step 202 by where the temperature of MOx sensor 102 has been set to a low temperature. The low temperature is a temperature below a threshold temperature such that ozone reacts to reduce the concentration of ozone in a gas in contact with the MOx sensor 102. In some embodiments, the threshold temperature may be between about 15 C and 150 C, although higher or lower threshold temperatures may be used in some embodiments. The threshold temperature set low enough to effectively reduce the ozone concentration in the gas sample exposed to MOx sensor 102, for example less than 100 C. As explained above, the low temperature is attained by setting power to heater 104 appropriately to achieve the low temperature at MOx sensor 102. In some embodiments, the temperature of MOx sensor 102 may be separately monitored, for example with temperature sensor 112. In some embodiments, the temperature of MOx sensor 102 may be calibrated with the power supplied to heater 104 such that the temperature is known from the power settings from heater driver 116.

In step 204, the low temperature is held for a period of time sufficient to reduce the ozone concentration in the gas in contact with MOx sensor 102. In some embodiments, the period of time is sufficient to reduce the ozone concentration below a threshold concentration. In some embodiments, the time is sufficient to reduce the ozone concentration below a threshold concentration (e.g. 10 ppb). In some embodiments, the time is sufficient to reduce the ozone concentration by a particular percentage amount. In some embodiments, the time period may be between 1 and 10 sec, for example 4 sec.

In step 206, the temperature of MOx sensor 102 is increased to an operating temperature. In some embodiments, the operating temperature can be between, for example, 100° C. and 500° C. In some embodiments, a single operating temperature is used. In some embodiments, data is taken through a range of operating temperatures as the temperature of MOx sensor 102 is traversed through the data collection range.

In step 208, the operating temperature and resistance data of MOx sensor 102 is acquired. In some embodiments, multiple data points are taken during data acquisition step 208. In some embodiments, a single or small number of data points can be acquired. In step 210, after the resistance data has been acquired, the temperature may be reduced to the low temperature as described above. In step 212, the resistance data is processed to supply results related to the gas sample. The results may include one or more of TVOC determinations, eCO2 determinations, or IAC determinations. As discussed above, in some embodiments, the results may be obtained by processing through an AI as illustrated in FIG. 1C.

In steps 204, 206, 208, and 210, process 200 can follow a temperature profile that controls the temperature at MOx sensor 102. In accordance with embodiments of the present disclosure, the temperature profile followed in steps 204, 206, 208, and 210 includes a low temperature period during which the ozone concentration of the gas sample being measured at MOx sensor 102 is reduced.

Figure 3A:
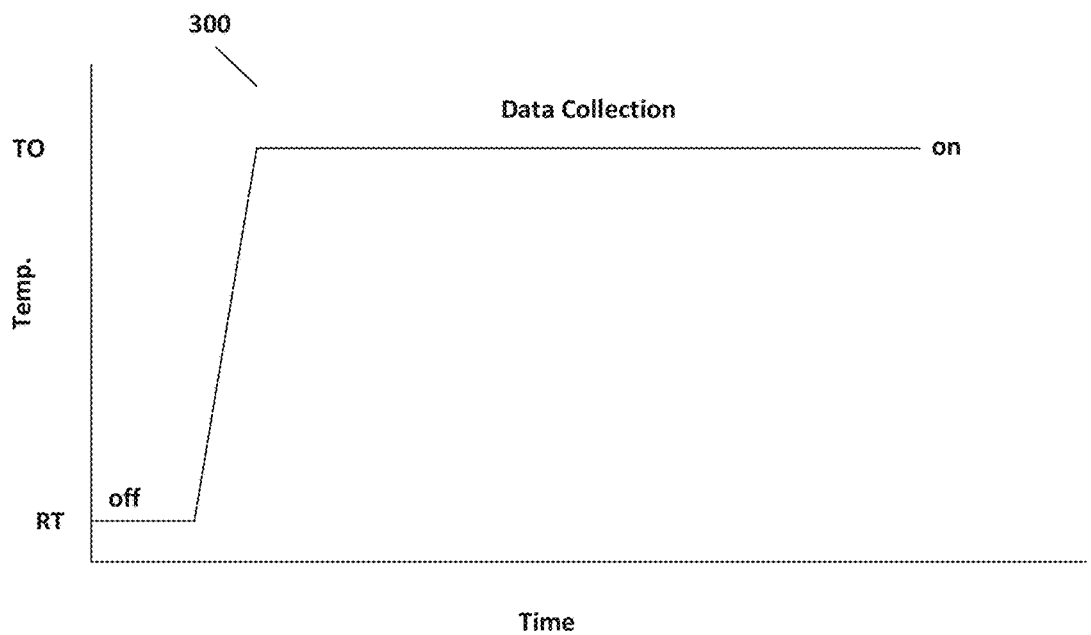
FIG. 3A illustrates a conventional temperature profile for operation of a gas sensor.

FIG. 3A illustrates a conventional temperature profile 300 for operation of gas sensor 100. In that case, the temperature of MOx sensor 102 starts at room temperature RT where gas sensor 100 is off. The temperature T is then raised to an operating temperature TO, where it remains throughout the operation of gas sensor 100. The temperature returns to room temperature when gas sensor 100 is turned off. Using temperature profile 300 allows ozone concentrations to affect the resulting measurements.

Figure 3B:
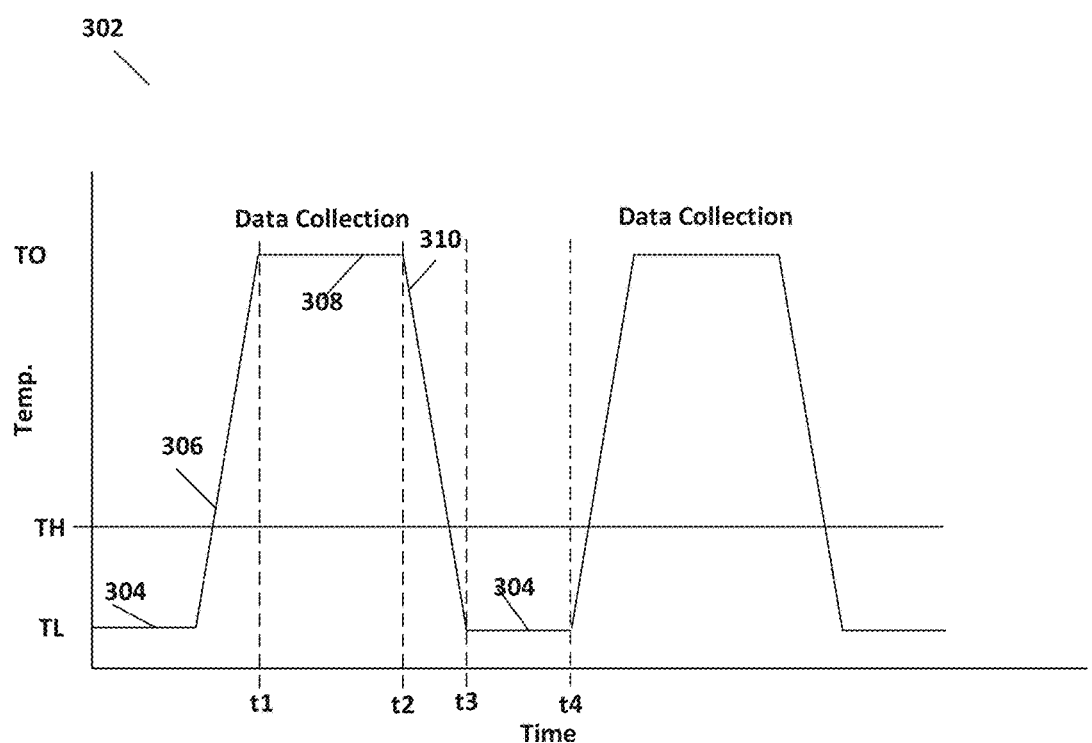
FIGS. 3B and 3C illustrates temperature profiles according to aspects of the present invention.

FIG. 3B illustrates a temperature profile 302 according to some embodiments of the present disclosure. Temperature profile 302 is often referred to as a low temperature algorithm. As illustrated in FIG. 3B, gas sensor 100 repeatedly cycles between a low temperature TL and an operating temperature TO. As illustrated in temperature profile 302 in FIG. 3B, in a data acquisition cycle the temperature of MOx sensor 102 is raised in temperature increase 306 to an operating temperature TO at the first time t1 of data collection time period 308. The data collection time period 308 is between times t1 and t2, during which resistance data from MOx sensor 102 is acquired. As discussed above, the operating temperature TO can be set, for example, between 100 and 500° C. At time t2, the temperature of MOx sensor 102 is reduced to the low temperature TL in profile period 310. In some embodiments, this may be accomplished by simply turning power off to heater 104 and allowing MOx sensor 102 to be cooled until low temperature TL is reached. As discussed above, TL can be any temperature below a threshold temperature TH below which ozone concentrations are reduced. At the low temperature TL, the ozone reacts and the concentration of ozone in the gas sample in contact with MOx sensor 102 is reduced. The low temperature TL is held in period 304 between times t3 and t4. The time period 304 is of sufficient time to allow reduction of the ozone concentration, for example to a level below a threshold ozone concentration or by a percentage amount. At time t4, at the end of period 304, a new data acquisition cycle is started by raising the temperature of MOx sensor 102 to the operating temperature TO.

Figure 3C:
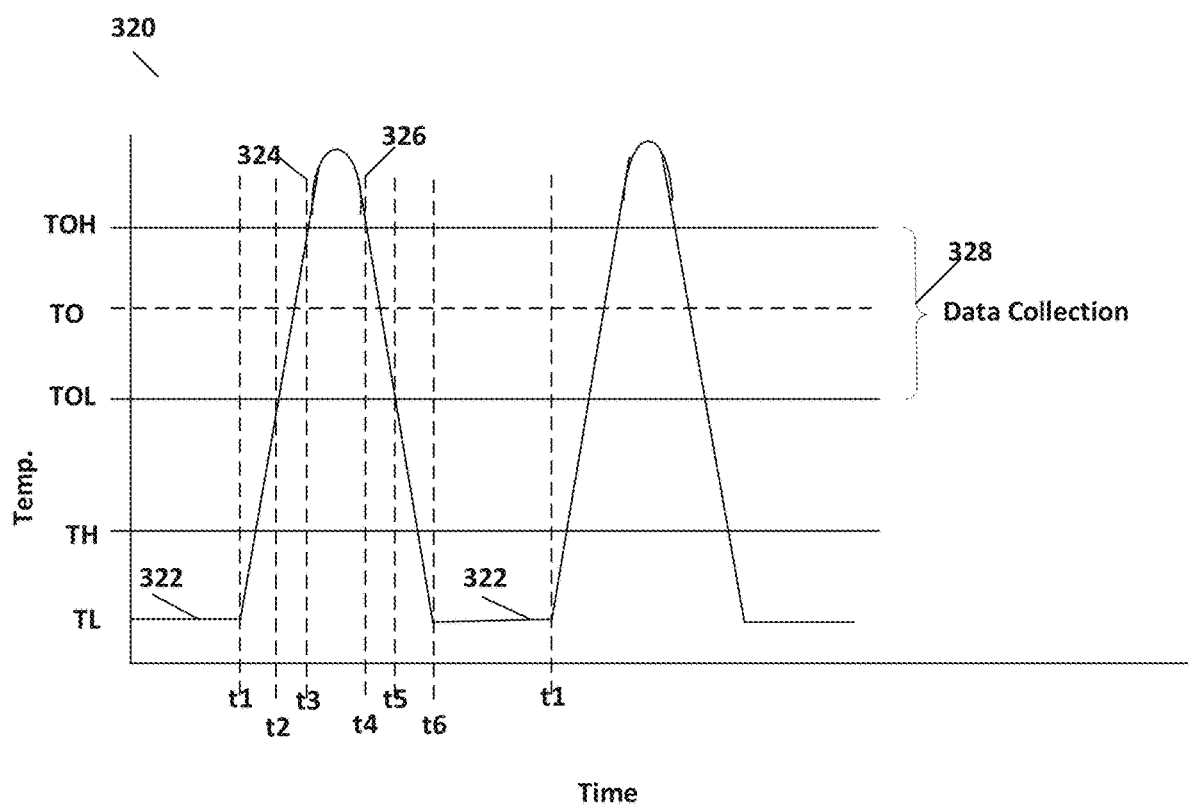

FIG. 3C illustrates another temperature profile 320 according to some embodiments. As illustrated in FIG. 3C, in period 322 the temperature of MOx sensor 102 is held at a low temperature TL that is below a threshold temperature TH as discussed above. At the beginning of a data collection group, at t1, the temperature of MOx sensor 102 is increased in period 324 through a data collection range 328. In particular, in temperature profile 320, in period 322 the temperature of MOx sensor 102 is held at temperature TL. At time t1, a data collection cycle begins with heating period 324. When the temperature of MOx sensor 102 reaches a low operating temperature TOL, data collection range 328. Resistance data and temperature data is acquired in step 208 at a plurality of temperatures while the operating temperature TO is increased from TOL at time t2 to a high operating temperature TOH at time t3. After data collection range 328 has been traversed. As illustrated in FIG. 3C, the temperature of MOx sensor 102 traverses data collection range 328 again as MOx sensor 102 cools between times t4 and t5. Gas sensor 100 may acquire further data points at a plurality of temperatures during times t4 and t5 as well. At time t6, the temperature of MOx sensor 102 has again cooled to the low temperature TL in order to reduce the ozone concentration for the next data collection cycle.

As illustrated, temperature profile 302 illustrated in FIG. 3B and temperature profile 320 illustrated in FIG. 3C cycles periodically so that the air in contact with MOx sensor 102 is sampled periodically. In some embodiments, the periodicity of temperature profile 302 and temperature profile 320 may be between 0.1 and 100 seconds, for example 1 to 100 seconds. In some embodiments, a long low temperature phase with a short data acquisition phase is included. For example, in some embodiments the temperature profile includes 90 seconds of low temperature with 1 sec for data acquisition for a 91 second periodicity. The periodicity and temperature portfolio can provide for any length of low temperature phase followed by a data acquisition phase. In some embodiments, with temperature profile 320 illustrated in FIG. 3C, the resistance versus temperature data acquired within data collection region 328 may allow determination of concentrations of individual gas concentrations in the air sample. Otherwise, better calculations of IAQ, TVOC, or eCO2 can be obtained as discussed above.

In the following description, gas sensors are tested to demonstrate aspects of the present disclosure. In general, a gas sensor 100 can be housed in a measurement chamber and gasses with various concentrations of ozone and concentrations of VOCs can be input. The gas concentrations can be determined by gas sensor 100 using conventional temperatures profiles and temperature profiles according to embodiments of the present disclosure. The gas concentrations can be determined by other determinations.

Figure 4:
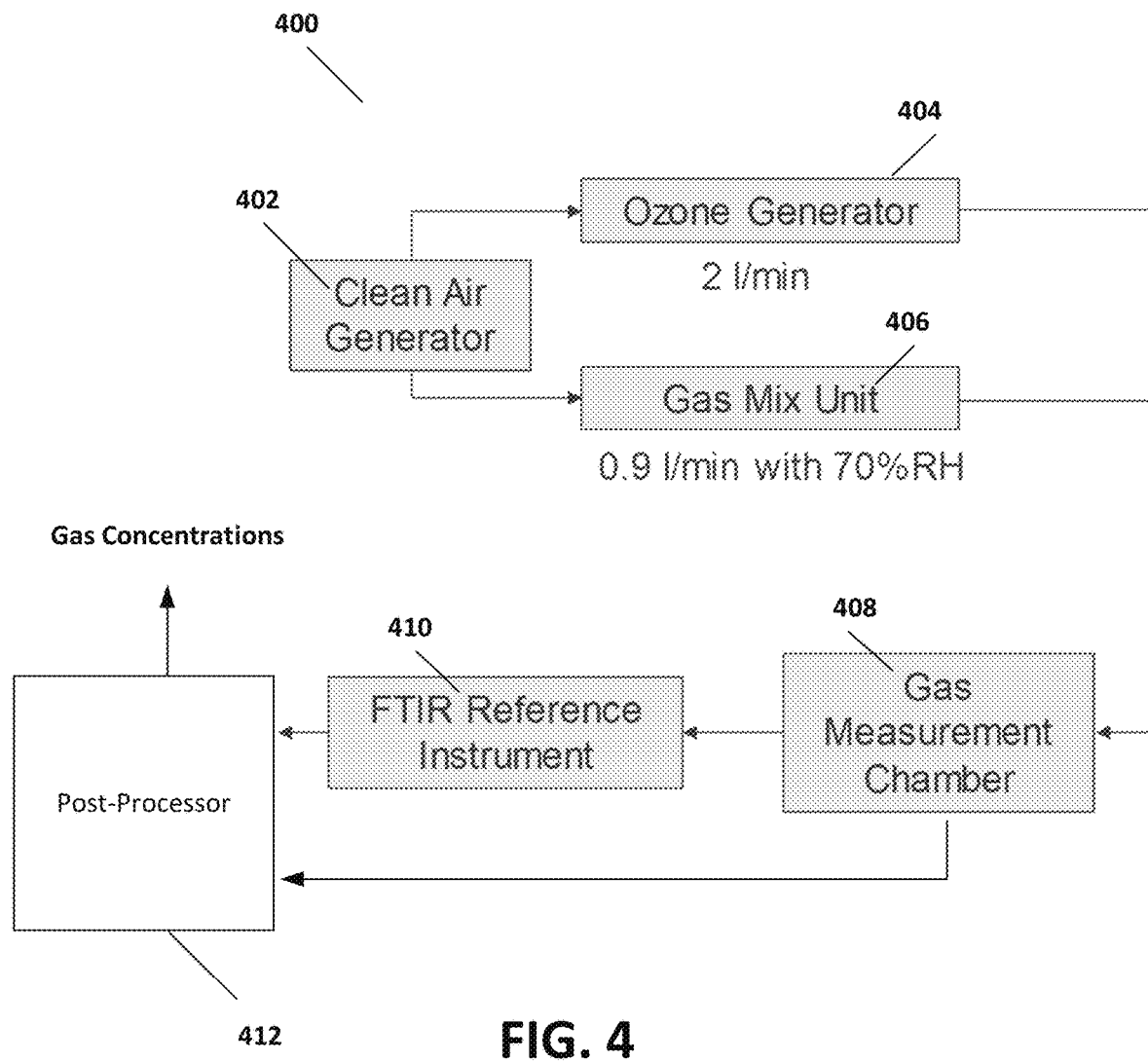
FIG. 4 illustrates a test system to test a gas sensor such as that illustrated in FIGS. 1A through 1C.

FIG. 4 illustrates a test system 400 that is used to test a gas sensor 100 such as that illustrated in FIG. 1. Clean air generator 402 can provide a source of clean air. Ozone generator 404 can provide a source of ozone. Gas mixing unit 406 can provide other gasses such as VOCs to the gas mixture. The mixed gas can be provided to a chamber 408, in which gas sensor 100 is provided. The gas can then be provided to a Fourier-Transform Infrared Spectrometer 410 that can provide a highly accurate measurement of the gas concentrations. A processing unit 412, which may be a computer system, receives processed data from gas sensor 100 in gas measurement chamber 408 and precise gas concentration data from FTIR instrument 410. Further, in some embodiments, processing unit 412 can control operation of clean air generator 402, ozone generator 404, and gas mix unit 406 to provide testing for gas sensor 100. The system 400 shown in FIG. 4 can be used to provide gasses to test the response of gas sensor 100 under both conventional practices and processes according to embodiments of the present disclosure.

Figure 5:
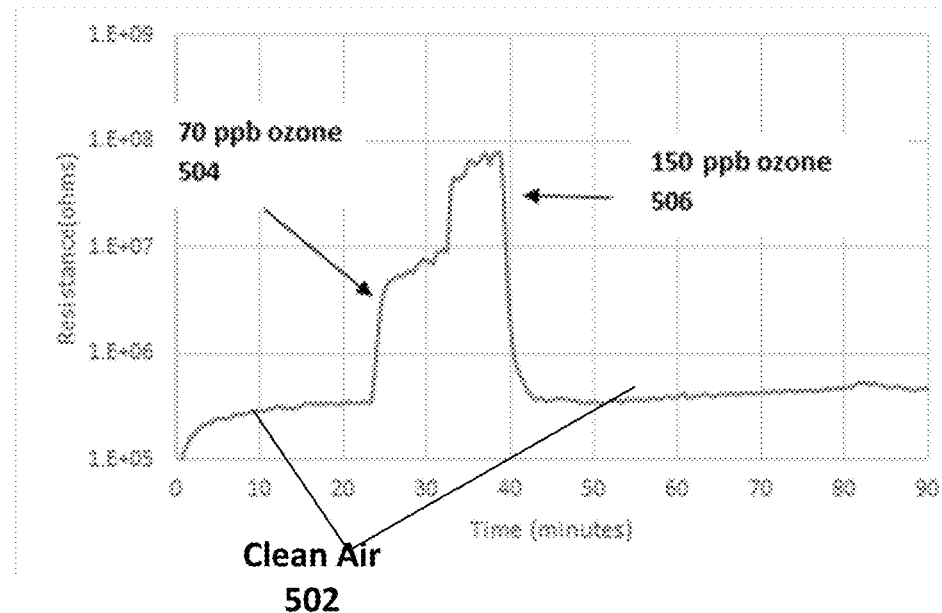
FIG. 5 illustrates resistance measurements in a gas sensor using standard operation such as that illustrated in FIG. 3A.

FIG. 5 illustrates resistance measurements in a gas sensor 100 placed in gas measurement chamber 408 of test system 400 under standard operation as illustrated by the temperature profile illustrated in FIG. 3A. In particular, FIG. 5 illustrates the measured resistance of MOx sensor 102 as a function of time 500 in the presence of clean air generated by clean air generator 402 (region 502), with 70 ppb ozone as added by ozone generator 404 (region 504), and 170 ppb ozone as added by ozone generator 404 (region 506). As illustrated in FIG. 5, the resistance of MOx sensor 102 increases by up to 3 orders of magnitude upon addition of 70 ppb of ozone in region 504 and by up to 4 orders of magnitude when the ozone concentration is increased to 170 ppb ozone in region 506.

Figure 6:
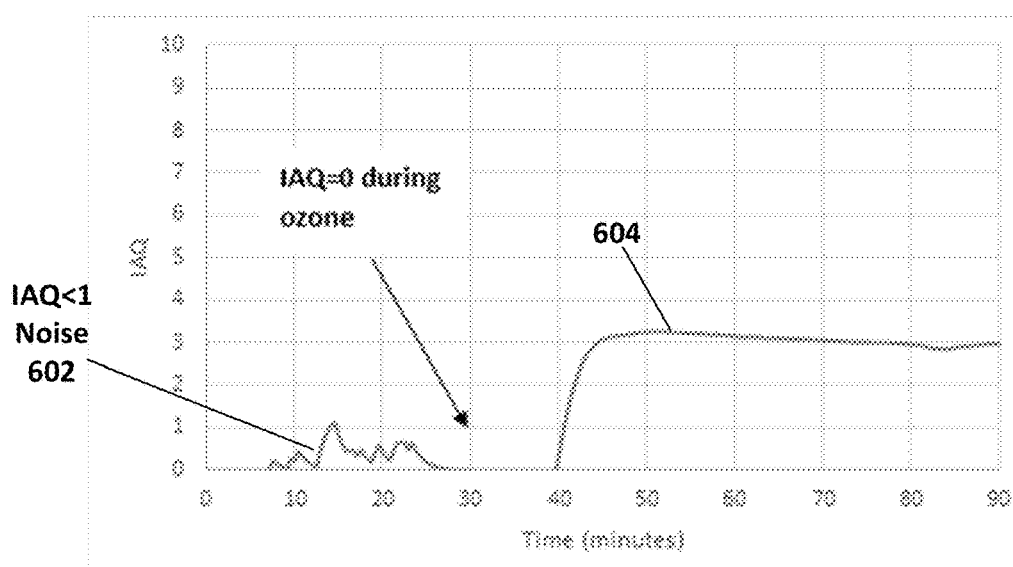
FIG. 6 illustrates an air quality measurement in a gas sensor under standard operation using the existing algorithm such as that illustrated in FIG. 3A.

FIG. 6 illustrates an air quality measurement as a function of time gas sensor 100 while under test in test chamber 408 of test system 400 under standard operation with temperature profile as illustrated in FIG. 3A. As illustrated, as a function of time, the IAQ went from less than 1 in the presence of clean air in region 602 up to an IAQ of 4 in the presence of ozone in region 604.

Figure 7:
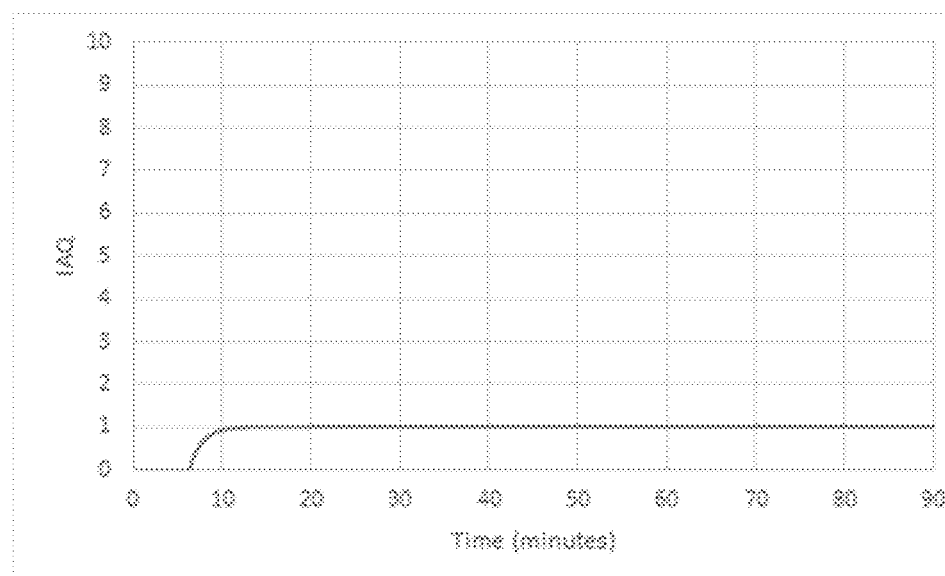
FIG. 7 illustrates an air quality measurement with an algorithm according to an embodiment of the present invention.

FIG. 7 illustrates an air quality measurement as a function of time in a gas sensor 100 while under test in test chamber 408 of test system 400 with an algorithm according to an embodiment of the present invention such as occurs with temperature profiles illustrated in FIG. 3B or 3C. As is illustrated, the air quality measurement is flat at an IAQ of 1 even in the presence of ozone, which was injected during the test period.

Figure 8A:
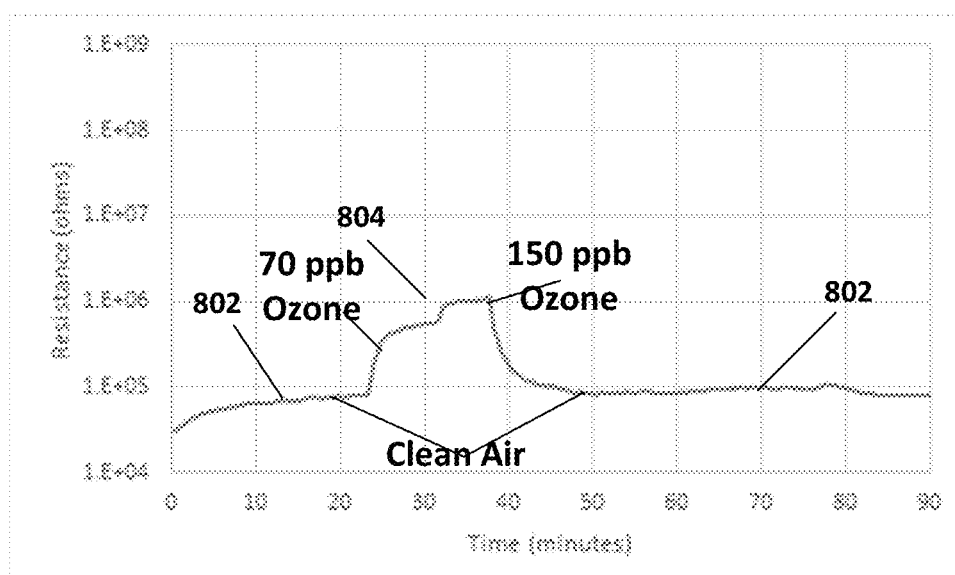
FIGS. 8A and 8B illustrates the resistance measurements of a gas sensor with when ozone is introduced with and without operation of an algorithm according to the present disclosure.

FIG. 8A illustrates the resistance as a function of time of a gas sensor 100 in test chamber 408 of test system 400 using a low power operation with and without ozone. As illustrated, in region 802 clean air is entered into test chamber 408 while in region 804 ozone is mixed with the clean air and entered into test chamber 408. As a result of the ozone, the resistance of MOx sensor 102 is increased, affecting the operation of gas sensor 100 as discussed above.

Figure 8B:
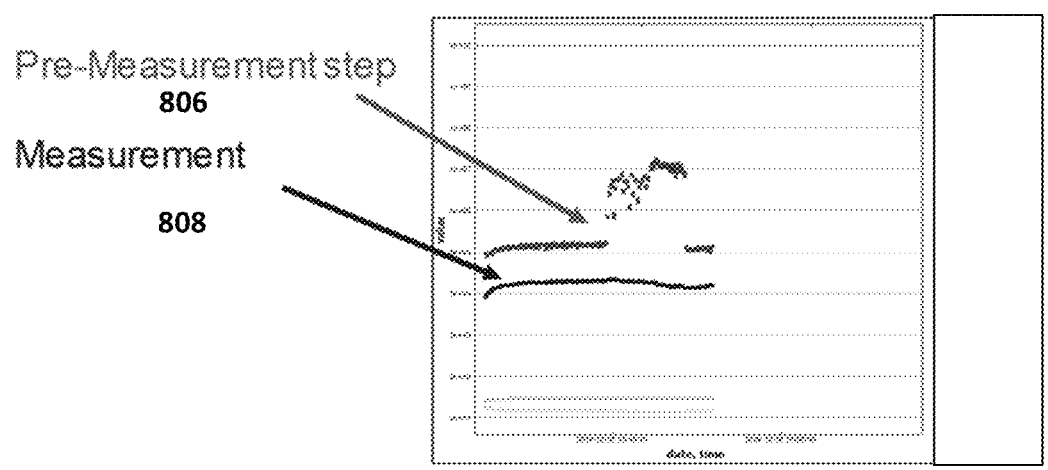

FIG. 8B illustrates the results of operation according to aspects of the present invention. FIG. 8B illustrates resistance as a function of time of a gas sensor 100 in test chamber 408 of test system 400 using a low temperature step according to a temperature profile according to aspects of the present disclosure, for example the temperature profiles illustrated in FIG. 3B or 3C. As illustrated, trace 806 illustrates a pre-measurement step at a low temperature, where the ozone can be reacted in a low power early stage. Trace 808 illustrates a measurement step after the pre-measurement step.

Figure 9A:
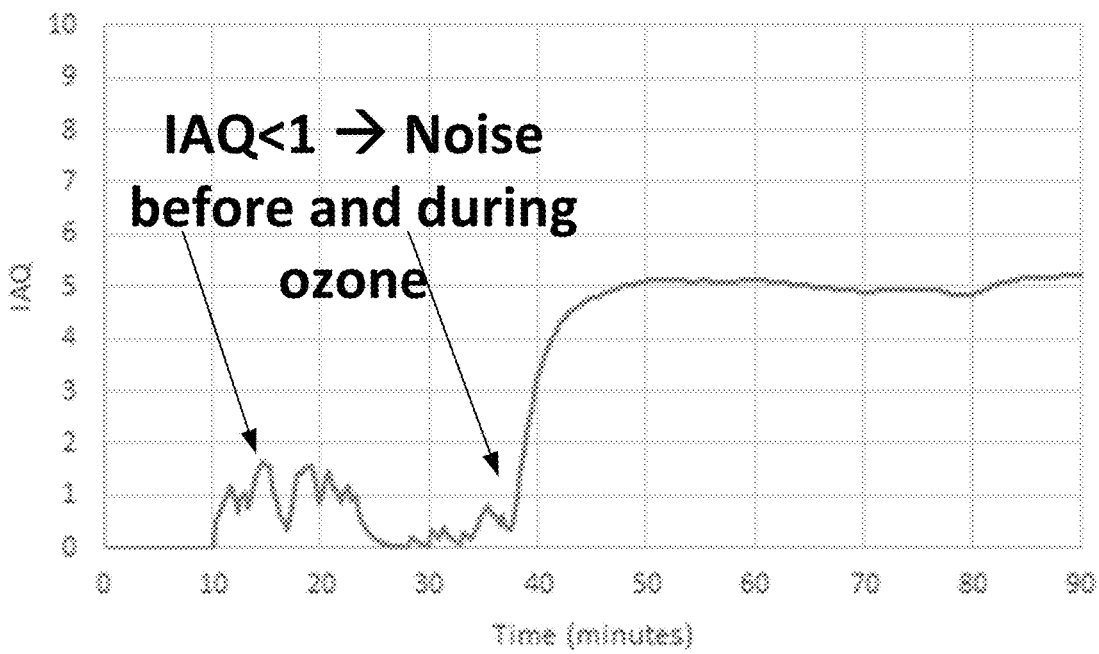
FIGS. 9A and 9B illustrates ozone reaction in an air quality measurement with and without operating an algorithm according to some embodiments of the present disclosure.
Figure 9B:
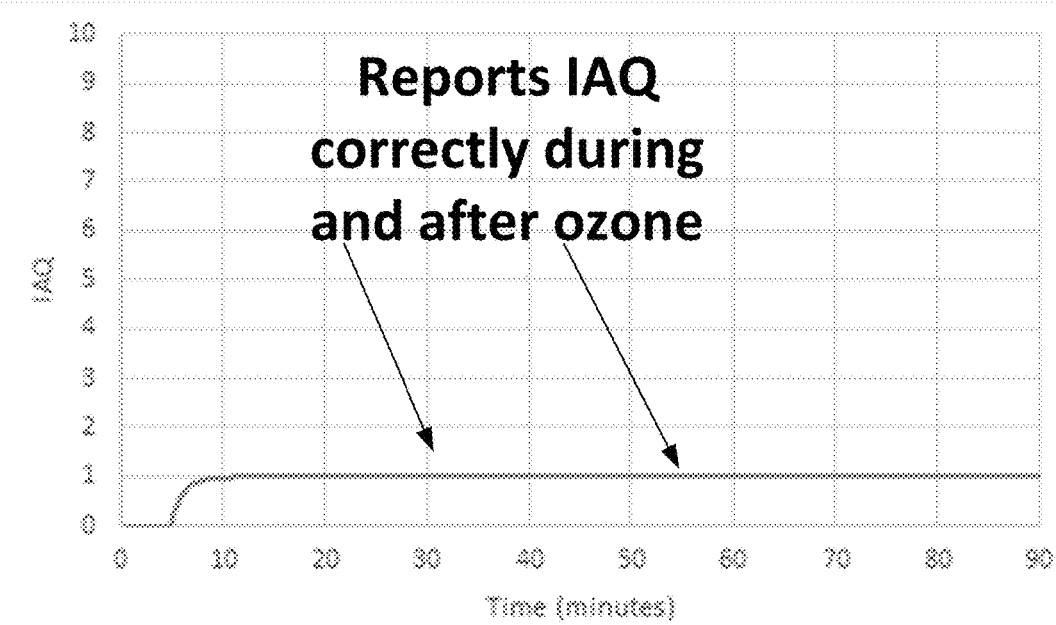

FIGS. 9A and 9B illustrate air quality measurements using a gas sensor 100 in test chamber 408 of test system 400 with a standard low-power algorithm (e.g., with the temperature profile as illustrated in FIG. 3A) and with an algorithm according to embodiments according to the present disclosure (e.g., with a temperature profile such as that illustrated in FIG. 3B or 3C), respectively. As illustrated, in FIG. 9A, the existing algorithms lead to an offset of the air quality measurement while the algorithm according to the present disclosure as illustrated in FIG. 9B shows no such offset.

Figure 10A:
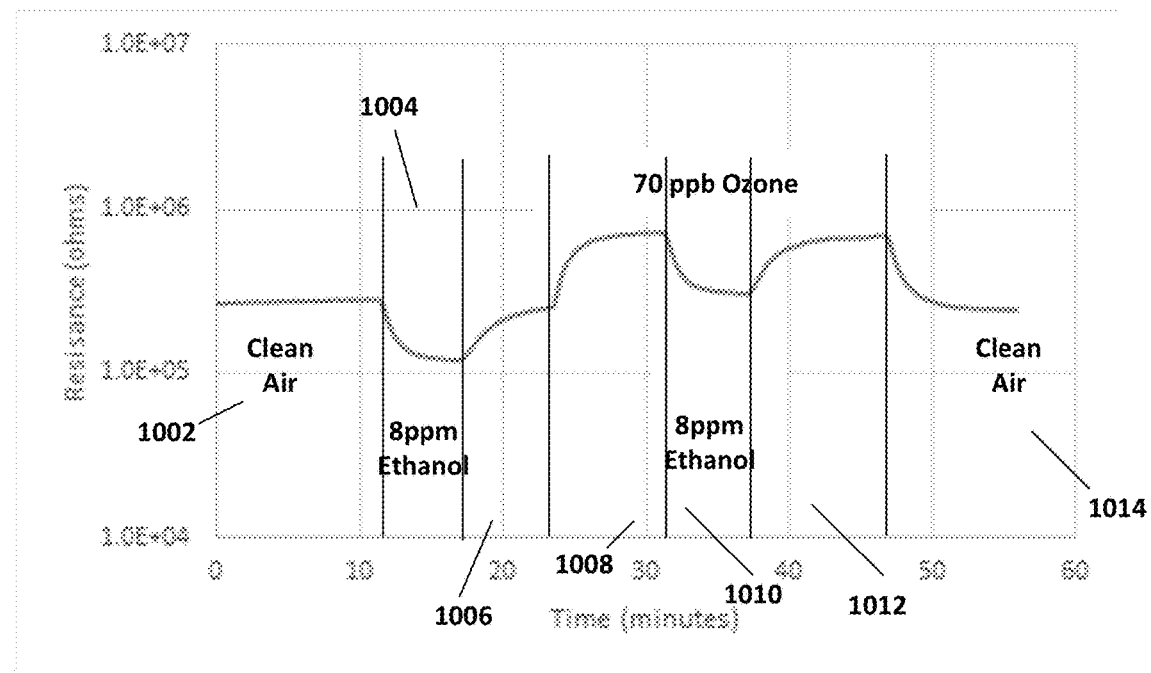
FIGS. 10A through 10C illustrate operation of a gas sensor with a low-temperature algorithm during the presence of ozone and VOCs according to some embodiments of the present disclosure.
Figure 10B:
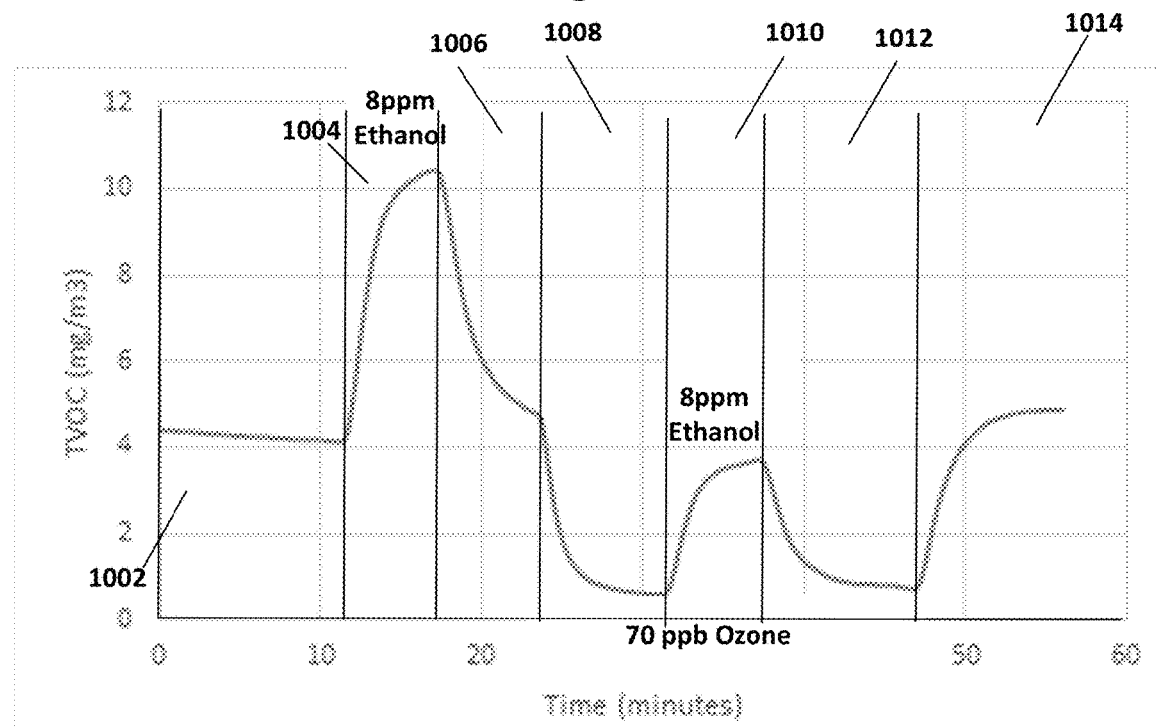
Figure 10C:
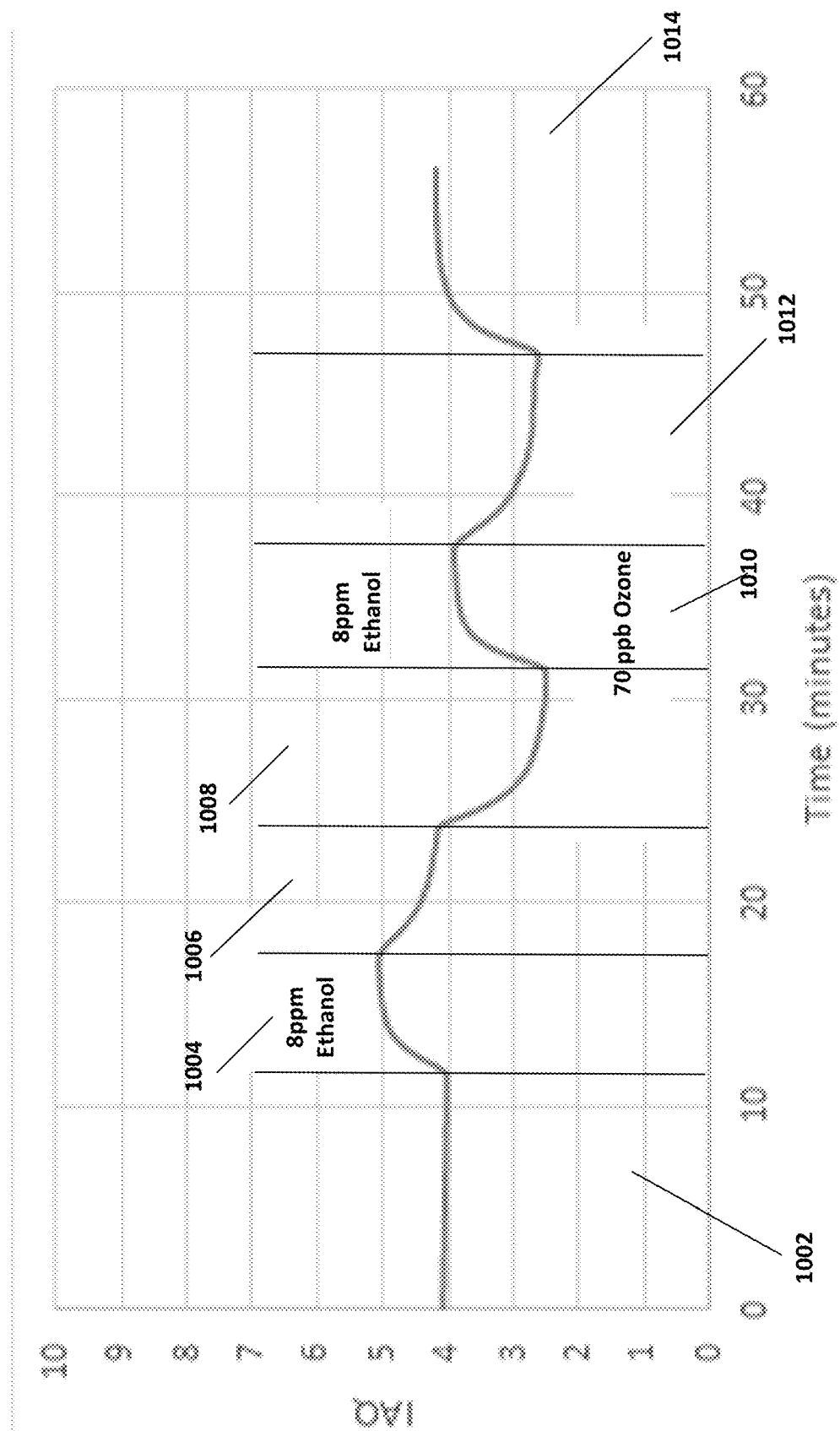

FIGS. 10A, 10B, and 10C further illustrate testing of a gas sensor 100 using a low-power algorithm according to some embodiments such as that illustrated in FIG. 3B. Gas sensor 100 is placed in test chamber 408 of test system 400 where clean air, ozone, and a VOC can be provided. FIG. 10A illustrates the resistance of MOx sensor 102 as a function of time is provided. FIG. 10B illustrates TVOC concentration as a function of time. FIG. 10C illustrates IAQ as a function of time. In each of FIGS. 10A, 10B, and 10B clean air, clean air with 8 ppm Ethanol, clean air with ozone, and clean air with a mixture of ozone and 8 ppm ethanol is provided. In particular, in a first period 1002 clean air is provided to gas sensor 100; in period 1004 clean air with 8 ppm ethanol is provided to gas sensor 100; in period 1006 clean air is provided to gas sensor 100; in period 1008 clean air with 70 ppb ozone is provided to gas sensor 100; in period 1010 clean air with 70 ppb ozone and 8 ppm ethanol is provided to gas sensor 100; in period 1012 clean air and 70 ppb ozone is provided to gas sensor 100; and in period 1014 clean air is provided to gas sensor 100. As is viewed in comparison with conventional algorithms, the effects of ozone on the resulting measurements is reduced.

FIG. 10A illustrates resistance as a function of time using with the low power operation as illustrated in FIG. 3B with and without the presence of ozone and ethanol as described above. As illustrated, the resistance drops in period 1004 with the introduction of 8 ppm ethanol. In period 1006, the resistance returns to the resistance levels illustrated in period 1002. In period 1008, with the introduction of ozone, the resistance increases. When ethanol is provided again in period 1010, the resistance is reduced again. In period 1012, when the ethanol is removed, the resistance returns to that of period 1008. When the ozone is removed in period 1014, the resistance returns to the resistance levels provided in period 1002. The following table provides the sensitivity to ethanol with and without the presence of ozone for several gas sensors such as gas sensor 100. These measurements indicate that the presence of ozone provides a constant resistance offset in the gas sensor.

|  | 8 ppm Ethanol Sensitivity | |
|---|---|---|
|  | 0 ppb O3 | 70 ppb O3 |
| Gas Sensor 1 | 2.8 | 2.8 |
| Gas Sensor 2 | 2.3 | 2.4 |
| Gas Sensor 3 | 2.5 | 2.4 |

FIG. 10B illustrates TVOC detection at low power operation such as that illustrated in FIG. 3B with and without the presence of ozone, during the same periods as indicated above. As indicated in FIG. 10B, the TVOC measurement is around 4 mg/m3 during period 1002 and increases to 10-12 in period 1004. The TVOC concentration starts returning to 4 in period 1006, but is dramatically decreased in period 1008 when ozone is introduced. The TVOC measurement increases again with introduction of ethanol in period 1010, and returns to near 0 during period 1012. The concentration returns to 4 in period 1014 when ozone is again turned off. The following table provides measured ethanol sensitivities with and without the presence of ozone for a number of different gas sensors such as gas sensor 100. As can be seen, ozone leads to underreporting of the ethanol concentration, probably due to VOC reduction.

|  | 8 ppm Ethanol TVOC (ppm) | |
|---|---|---|
|  | 0 ppb O3 | 70 ppb O3 |
| Gas Sensor 1 | 6.5 | 1.8 |
| Gas Sensor 2 | 5.2 | 1.9 |
| Gas Sensor 3 | 5.3 | 2.1 |

FIG. 10C illustrates another TVOC detection with a low power operation according to some embodiments with and without the presence of ozone. The ethanol and ozone concentrations in periods 1002, 1004, 1006, 1008, 1010, 1012, and 1014 is defined above. The following table provides measured ethanol sensitivities with and without the presence of ozone. Again, this demonstrates that ozone leads to underreporting.

|  | 8 ppm Ethanol TVOC (ppm) | |
|---|---|---|
|  | 0 ppb O3 | 70 ppb O3 |
| Gas Sensor 1 | 6.5 | 1.8 |
| Gas Sensor 2 | 5.2 | 1.9 |
| Gas Sensor 3 | 5.3 | 2.1 |

Figure 11:
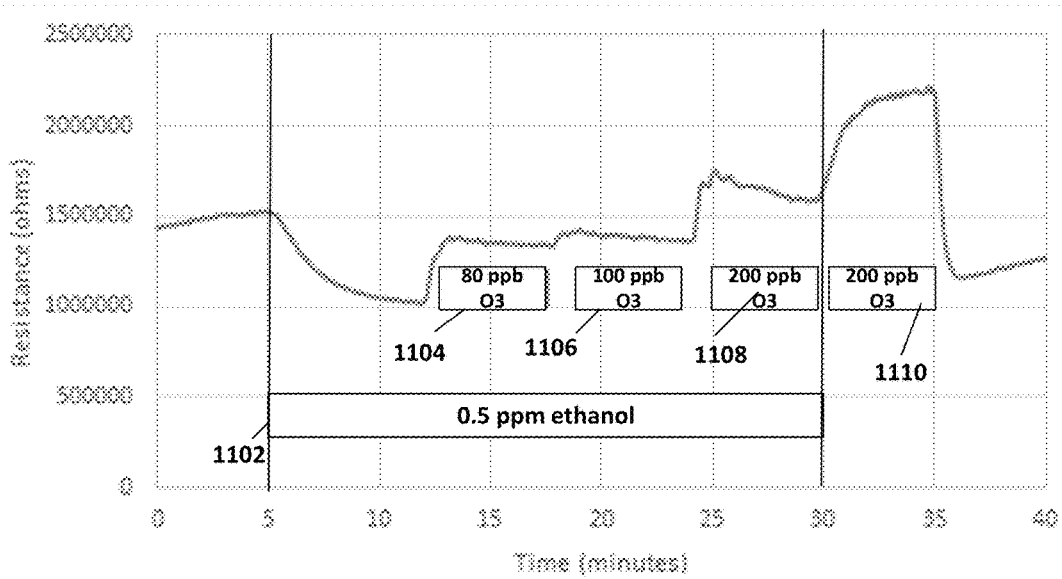
FIG. 11 illustrates resistance as a function of time with various ozone concentrations and other gasses present.

FIG. 11 illustrates resistance as a function of time with various ozone concentrations and with addition of ethanol. In particular, in FIG. 11, during period 1102 0.5 ppm ethanol is introduced to test chamber 408 in which gas sensor 100 is placed. Gas sensor 100 is executed a conventional low temperature process with neural network processing. During period 1104, which overlaps with period 1102, 80 ppb of ozone is introduced. In period 1106, which overlaps with period 1102, 100 ppb ozone is introduced. In period 1108, which overlaps with period 1102, 200 ppb ozone is introduced. In period 1110, which occurs after period 1102, 200 ppb ozone is introduced. This is an illustration of function of a neural network sequence, which helps to mitigate the effects of ozone. As is illustrated, resistance decreases during TVOC concentrations. Further, the presence of ozone gives an (even lower) offset, but TVOC can still be detected in each case. However, there is still resistance offsets due to the presence of ozone.

Figure 12:
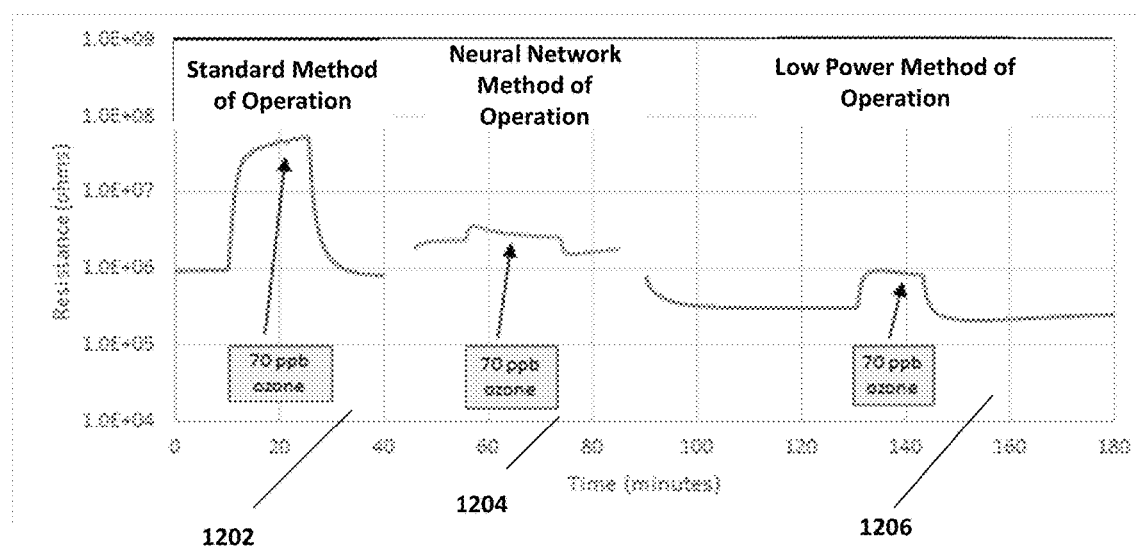
FIG. 12 illustrates operation according to embodiments of the present invention.

FIG. 12 illustrates operation according to embodiments of the present invention. Specifically outlined is ozone response in the resistance during a standard operation 1202, neural network method of operation 1204, and low power method of operation 1206 according to some embodiments. As is illustrated, both utilization of neural network processing and application of a low-power algorithm according to some embodiments reduce the effects of ozone on operation of gas sensor 100.

Figure 13:
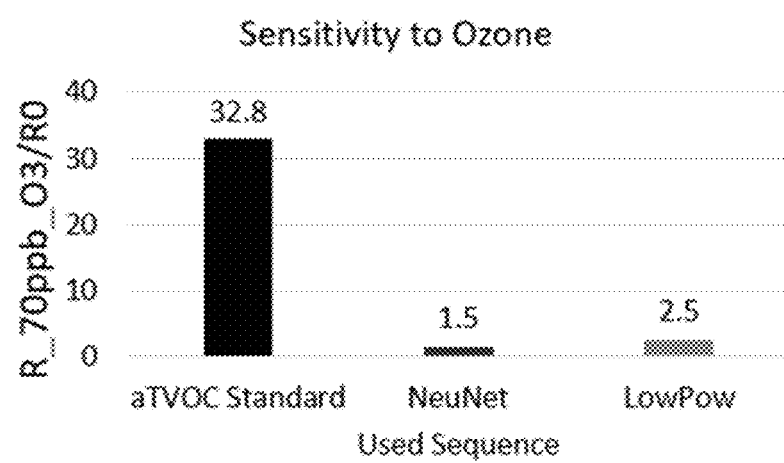
FIG. 13 illustrates the sensitivity to ozone with embodiments of the present invention in comparison with standard algorithms.

FIG. 13 illustrates the sensitivity to ozone with embodiments of the present invention in comparison with standard algorithms.

In summary, the standard method of operation leads to large increase in MOx resistance during an ozone event. Embodiments of the new algorithm according to the present invention, however, allows the baseline to be under control during ozone events, leads to more accurate TVOC readings after the ozone event. Additionally, VOC is still detectable during the ozone event (in case of presence). These embodiments provide the correct algorithm output after the ozone event for IAQ, TVOC, and eCO2 measurements.

Consequently, as is demonstrated above, a lower temperature step in the sequence will lead to an ozone reaction, reducing the amount of ozone present in the gas sample. For the low temperature process, a sequence including a period of low temperature operation can be provided instead of running the gas sensor at a constant operating temperature. For example, typical MOx gas sensors are operated between 250° C.-350° C. In the low temperature portion of the sequence, the temperature can be lowered to around ambient temperature (e.g. around 150° C. for a period of time sufficient to allow the reaction to substantially complete.

In some embodiments, a Neural Network approach can be used to further refine the sequence. The Neural Network temperature profile can be used to affect the present invention. The baseline (highest resistance in clean air) can be limited to a low Mega-Ohm number and a damping filter can be used to check if ozone is present. When ozone is present, the metal oxide resistance will immediately rise from the Kilo-Ohm to Mega and Giga-Ohm ranges. This this approach, the ozone events can be filtered to provide more accurate readings after the ozone event.

The above detailed description is provided to illustrate specific embodiments of the present invention and is not intended to be limiting. Numerous variations and modifications within the scope of the present invention are possible. The present invention is set forth in the following claims.

What is claimed is:

1. A method of operating a gas sensor, comprising:
    setting power to a heater in contact with a MOx sensor to provide a temperature that is at a low temperature below a threshold temperature below which an ozone concentration is reduced;
    holding the temperature at the low temperature below the threshold temperature for a period of time to reduce ozone concentration in a gas sample in contact with the MOx sensor;
    increasing power to the heater to increase the temperature of the MOx sensor to an operating temperature;
    acquiring resistance data from the MOx sensor at the operating temperature; and
    processing the resistance data to provide a result related the gas sample.

2. The method of claim 1, wherein the threshold temperature is between 15 C and 50 C.

3. The method of claim 1, wherein the period of time is between 0.1 and 100 sec.

4. The method of claim 1, wherein the operating temperature is a single temperature between 100 C and 500 C and acquiring resistance data includes measuring one or more data points at the single temperature.

5. The method of claim 1, wherein the operating temperature is a range of temperatures between a low operating temperature and a high operating temperature and acquiring resistance data includes measuring one or more data points while the operating temperature is in the range.

6. The method of claim 5, wherein acquiring resistance data includes measuring the one or more data points while the temperature is increasing and while the temperature is decreasing.

7. The method of claim 1, wherein the result is one or more of concentration of a volatile organic compound (VOC), concentration of total VOCs (TVOC), concentration of carbon dioxide (eCO2), and indoor air quality (IAQ).

8. The method of claim 7, wherein processing the resistance includes processing the result through a neural network to provide an adjusted result.

9. The method of claim 8, further including providing the adjusted result to an external device.

10. The method of claim 1, wherein the effect of ozone on the result is reduced.

11. A gas sensor, comprising:
    a MOx sensor;
    a heater in contact with the MOx sensor;
    a heater driver configured to control the heater; and
    a processor configured to receive resistance data from the MOx sensor, control the heater driver to control a temperature of the MOx sensor, and further configured to execute instructions to
        set power to the heater in contact with the MOx sensor to provide a temperature that is at a low temperature below a threshold temperature below which an ozone concentration is reduced;
        hold the temperature at the low temperature below the threshold temperature for a period of time sufficient to reduce ozone concentration in a gas sample to below a threshold concentration;
        increase power to the heater to increase the temperature to an operating temperature;
        acquire resistance data from the MOx sensor with the temperature at the operating temperature;
        reduce power to the heater to reduce the temperature to the low temperature below the threshold temperature; and process the resistance data to provide a result related the gas sample.

12. The gas sensor of claim 11, wherein the threshold temperature is between 15 C and 150 C.

13. The gas sensor of claim 11, wherein the period of time is between 0.1 to 100 sec.

14. The gas sensor of claim 11, wherein the operating temperature is a single temperature between 100 C and 500 C and acquiring resistance data includes measuring one or more data points at the single temperature.

15. The gas sensor of claim 11, wherein the operating temperature is a range of temperatures between a low operating temperature and a high operating temperature and acquiring resistance data includes measuring one or more data points while the operating temperature is in the range.

16. The gas sensor of claim 15, wherein acquiring resistance data includes measuring the one or more data points while the temperature is increasing and while the temperature is decreasing.

17. The gas sensor of claim 11, wherein the result is one or more of concentration of a volatile organic compound (VOC), concentration of total VOCs (TVOC), concentration of carbon dioxide (eCO2), and indoor air quality (IAQ).

18. The gas sensor of claim 17, wherein processing the resistance includes processing the result through a neural network to provide an adjusted result.

19. The gas sensor of claim 18, further including providing the adjusted result to an external device.

20. The gas sensor of claim 11, wherein the effect of ozone on the result is reduced.

* * * * *